US007784461B2

(12) United States Patent
Figueiredo et al.

(10) Patent No.: US 7,784,461 B2
(45) Date of Patent: Aug. 31, 2010

(54) THREE-DIMENSIONAL WAVEFORM DISPLAY FOR A BREATHING ASSISTANCE SYSTEM

(75) Inventors: David Luis Figueiredo, Fremont, CA (US); Michael K. Davis, Beaverton, OR (US); Mahesh K. Seetharaman, Dublin, CA (US); Gail Frances Upham, Fallbrook, CA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 1009 days.

(21) Appl. No.: 11/535,371

(22) Filed: Sep. 26, 2006

(65) Prior Publication Data

US 2008/0077033 A1 Mar. 27, 2008

(51) Int. Cl.
*A61M 11/00* (2006.01)
(52) U.S. Cl. ................... 128/204.23; 600/300
(58) Field of Classification Search .......... 600/529, 600/300, 301; 715/709, 810; 128/204, 204.23, 128/204.21, 204.22
See application file for complete search history.

(56) References Cited

U.S. PATENT DOCUMENTS 5,931,160 A * 8/1999 Gilmore et al. ........ 128/204.21
6,001,060 A * 12/1999 Churchill et al. ............ 600/300
6,273,855 B1 * 8/2001 Schmid et al. ............... 600/300
7,017,574 B2 * 3/2006 Biondi et al. .......... 128/204.21

FOREIGN PATENT DOCUMENTS

WO 99/47200 A 9/1999
WO 2005/067520 A 7/2005

OTHER PUBLICATIONS

International Search Report with Written Opinion, Jan. 9, 2008, 11 pages, PCT/US2007/079048.

* cited by examiner

*Primary Examiner*—Steven O Douglas

(57) ABSTRACT

An apparatus configured to display a three-dimensional representation of a waveform for a breathing assistance system may include a processor and a display device. The processor may be configured to receive signals from one or more sensors over a plurality of time periods and generate multiple instances of a waveform based on the received signals, each instance corresponding to one of the plurality of time periods. The display device may be configured to cooperate with the processor to display a graphical three-dimensional representation of the waveform over time. The three-dimensional representation may include graphical representations of the multiple instances of the waveform displayed simultaneously.

26 Claims, 2 Drawing Sheets

THREE-DIMENSIONAL WAVEFORM DISPLAY FOR A BREATHING ASSISTANCE SYSTEM

TECHNICAL FIELD

The present disclosure relates generally to the field of breathing assistance systems, e.g., three-dimensional waveform displays for a breathing assistance system.

BACKGROUND

Clinical treatment of a ventilated patient often requires that the breathing characteristics of the patient be monitored to detect the effects of a particular ventilation strategy on a patient or changes in the patient's breathing patterns. Many modern ventilators include a display that provides a visual display of various parameters regarding the patient's breathing patterns and/or the operation of the ventilator, and may allow the caregiver to adjust ventilator settings to select or adjust the ventilation strategy being implemented. For example, a ventilator may display one or more of the following parameters: airway pressure, exhaled volume, ventilation mode, type of breath, mean airway pressure, peak airway pressure, PEEP/CPAP pressure, plateau pressure, respiratory rate, I:E ratio, tidal volume, minute volume, and spontaneous minute volume.

In addition, some ventilators may display various waveforms indicating one or more parameters of the patient's breathing patterns and/or the operation of the ventilator over time, e.g., over a breath cycle. For example, such waveforms may include a flow-volume loop (which graphically depicts the flow of air compared to the total volume inspired or expired), and a pressure-volume loop (which graphically depicts the change in circuit pressure compared to the total volume inspired or expired).

SUMMARY

According to one embodiment of the disclosure, an apparatus configured to display a three-dimensional representation of a waveform for a breathing assistance system may include a processor and a display device. The processor may be configured to receive signals from one or more sensors over a plurality of time periods and generate multiple instances of a waveform based on the received signals, each instance corresponding to one of the plurality of time periods. The display device may be configured to cooperate with the processor to display a graphical three-dimensional representation of the waveform over time. The three-dimensional representation may include graphical representations of the multiple instances of the waveform displayed simultaneously.

According to another embodiment of the disclosure, a display device may be configured to display a graphical three-dimensional representation of a waveform over time. The three-dimensional representation may include graphical representations of multiple instances of the waveform displayed simultaneously. The multiple instances of the waveform may be generated based on signals from one or more sensors over a plurality of time periods, each instance corresponding to one of the plurality of time periods.

According to another embodiment of the disclosure, logic instructions may be encoded in computer-readable media executable by a processor. When executed, the logic instructions may be operable to receive signals from one or more sensors over a plurality of time periods; generate multiple instances of a waveform based on the received signals, each instance corresponding to one of the plurality of time periods; and cause the display of a graphical three-dimensional representation of the waveform over time. The three-dimensional representation may include graphical representations of the multiple instances of the waveform displayed simultaneously.

According to another embodiment of the disclosure, a breathing assistance device may be configured to display a three-dimensional representation of a waveform over time. The breathing assistance device may include processing means and display means. The processing means may be configured to receive signals from one or more sensors over a plurality of time periods, and generate multiple instances of a waveform based on the received signals, each instance corresponding to one of the plurality of time periods. The display means may be configured to cooperate with the processing means to display a graphical three-dimensional representation of the waveform over time. The three-dimensional representation may include graphical representations of the multiple instances of the waveform displayed simultaneously.

DETAILED DESCRIPTION OF THE DRAWING

Selected embodiments of the disclosure may be understood by reference, in part, to FIGS. 1-5, wherein like numbers refer to same and like parts. The present disclosure relates generally to displays for assisted breathing devices (e.g., a ventilator, CPAP device, or BiPAP device). In some embodiments, a display device for breathing assistance system may be configured to display a graphical three-dimensional representation of a waveform over time. The three-dimensional representation may include graphical representations of multiple instances of the waveform displayed simultaneously. The multiple instances of the waveform may be generated based on signals received from one or more sensors over a plurality of time periods, wherein each waveform instance corresponds to one of the plurality of time periods. In some embodiments, each waveform instance corresponds to one breath.

The waveform may comprise, for example, a loop or other waveform in which two parameters other than time are plotted against each other in two dimensions, e.g., a flow-volume loop or a pressure-volume loop. Multiple instances of the waveform may be displayed in a cascaded manner or otherwise aligned to indicate a third dimension representing time. For example, the most recent waveform instance may be displayed in front, the next most recent waveform instance may be displayed cascaded behind the most recent waveform, the next most recent waveform instance may be displayed cascaded behind that, and so on. Such a three-dimensional representation may provide a graphical indication of changes in the waveform over time.

In some embodiments, an average waveform may be calculated based on at least two waveform instances, and a corresponding average waveform graphic may be included in the three-dimensional waveform representation. The average waveform graphic may be automatically updated over time, and may be visually distinct from the individual waveform instances (e.g., the average waveform graphic may have a different color, brightness, line thickness, line type, or may be a dashed or flashing line). Similarly, in some embodiments, the most recent waveform instance in the three-dimensional waveform representation may be visually distinct from the other waveform instances (e.g., the average waveform graphic may have a different color, brightness, line thickness, line type, or may be a dashed or flashing line).

Figure 1:
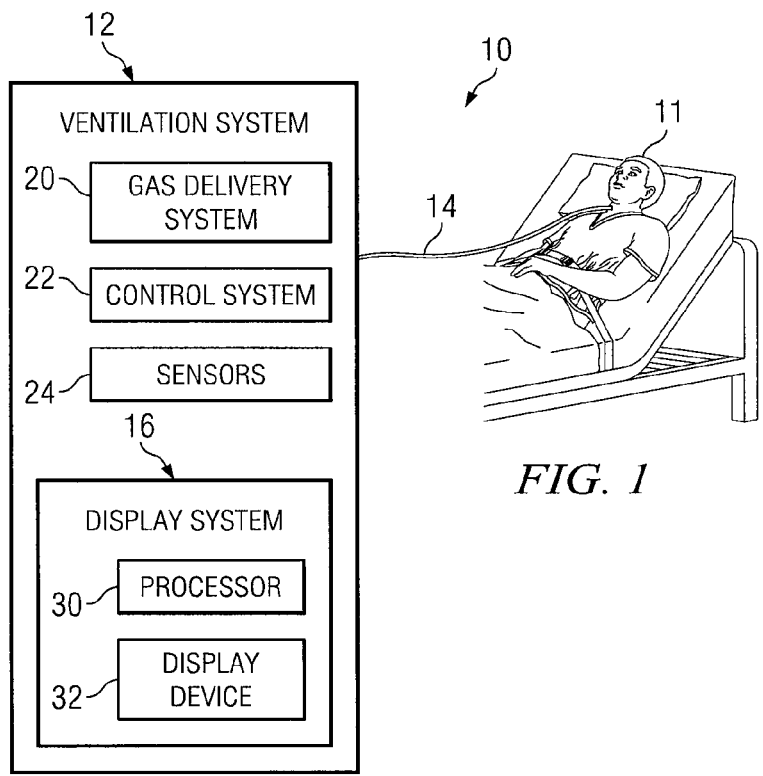
FIG. 1 illustrates an example breathing assistance system having an associated display device, according to one embodiment of the disclosure.

FIG. 1 illustrates an example breathing assistance system 10, according to one embodiment of the disclosure. Breathing assistance system 10 may be generally configured to provide breathing assistance (e.g., providing ventilation and/or treating an apnea or other breathing condition) to a patient 11. Breathing assistance system 10 may include a ventilation system 12, a connection system 14, and a display system 16.

Ventilation system 12 may comprise any device, apparatus, or system for delivering breathing gas to a patient, e.g., a ventilator, a respirator, a CPAP device, or a BiPAP device. Ventilation system 12 may include a gas delivery system 20, a control system 22, and one or more sensors 24. In addition, in some embodiments, ventilation system 12 may include display system 16, while in other embodiments, display system 16 may be distinct form ventilation system 12.

Gas delivery system 20 may include any device or devices configured to generate, supply, and/or deliver gas (e.g., pressurized air) toward patient 11 via mask apparatus 14. For example, ventilation system 12 may comprise a device capable of generating pressurized air (e.g., a motorized blower or piston-based device), a wall outlet through which pressurized air may be supplied (e.g., in a hospital or clinic), valves configured to control the supply of gas to the patient (e.g., a PSOL or other solenoid valve), one or more tanks of compressed gas, a compressor, or any other suitable source of pressurized or non-pressurized gas. As used herein, the term "gas" may refer to any one or more gases and/or vaporized substances suitable to be delivered to and/or from a patient via one or more breathing orifices (e.g., the nose and/or mouth), such as air, nitrogen, oxygen, any other component of air, $CO_2$, vaporized water, vaporized medicines, and/or any combination of two or more of the above, for example. As used herein, the term "patient" may refer to any person or animal that may receive breathing assistance from system 10, regardless of the medical status, official patient status, physical location, or any other characteristic of the person. Thus, for example, patients may include persons under official medical care (e.g., hospital patients), persons not under official medical care, persons receiving care at a medical care facility, persons receiving home care, etc.

Control system 22 may be operable to control gas delivery system 20 to control the delivery of gas to patient 11 based on various input received from a user (e.g., via a touch screen and/or other user interfaces provided by ventilation system 12) and/or data received from one or more sensors 24. For example, control system 22 may regulate the pressure and/or flow of gas delivered to a patient based at least on data received from sensors 24. Gas delivery control system 22 may include, or have access to, one or more processors, memory devices, and any other suitable hardware or software. The one or more memory devices may store instructions (e.g., any suitable software, algorithms, or other logic or instructions that may be executed by one or more processors) for controlling the operation of ventilation system 12, e.g., controlling the ventilation support provided by gas delivery system 20.

Sensors 24 may include any device or devices for sensing, detecting, and/or monitoring one or more parameters related to the ventilation of patient 11, e.g., parameters regarding the ventilation provided by ventilation system 12 and/or physiological parameters regarding patient 11. For example, sensors 24 may include one or more devices for measuring various parameters of gas flowing into or out of patient 11 or ventilation system 12, e.g., the pressure, flow rate, flow volume, temperature, gas content, and/or humidity of such gas flow. Thus, sensors 24 may include, e.g., one or more pressure sensors, flow meters, transducers, and/or oxygen sensors. Sensors 24 may be located at one or more various locations in breathing assistance system 10 for monitoring the pressure and or flow of gasses flowing into and/or out of patient 11 and/or ventilation system 12. For example, one or more sensors 24 may be located in or proximate ventilation system 12 and/or connection system 16. For example, depending on the particular embodiment, one or more sensors 24 may be located within or proximate to ventilation system 12, an inspiration conduit and/or exhalation conduit of a patient circuit, an artificial airway, and/or a Wye connector.

Connection system 14 may be generally configured to deliver gas from ventilation system 12 to patient 11 and/or to remove exhaust gas away from patient 11. For example, connection system 14 may comprise any suitable type of breathing circuit (e.g., a single-limb or dual-limb circuit) and/or a patient connection apparatus. The patient connection apparatus may include any device or devices configured to connect the breathing circuit to one or more breathing passageways of patient 11. For example, the patient connection apparatus may include a patient connection tube directly connected to the patient's trachea, an artificial airway (e.g., an endotracheal tube or other device) inserted in the patient's trachea, and/or a mask, cushion or nasal pillows positioned over the patient's nose and/or mouth. In embodiments including a patient connection tube, the patient connection tube may include a Wye (or "Y") connector.

Display system 16 may be operable to display various data regarding patient 11, the operation of ventilation system 12, the ventilation of patient 11, and/or any other relevant data. Display system 16 may be fully or partially integrated with ventilation system 12. In some embodiments, display system 16 may be part of or otherwise associated with, a graphic user interface, which may be configured to display various information and/or provide an interface (e.g., a touch screen) for accepting input from human operators (e.g., to set or modify ventilation settings, to access data, to change or configure the display, to select and/or modify 3-D waveform representations, etc.).

Display system 16 may include a processor 30, a display device 32, and any other suitable components. Processor 30 may include any system or device for executing code or logic instructions (e.g., software or firmware) for controlling display device 32, such as a microcontroller, a digital signal processor (DSP), an application specific integrated controller (ASIC), electrically-programmable read-only memory (EPROM), or a field-programmable gate array (FPGA), for example. Processor 32 may be the same processor used for control system 22, or may be a separate processor.

Display device 32 may comprise any type of screen or other visual display for displaying data regarding the patient's breathing patterns and/or the operation of ventilation system 12. For example, display device 32 may display any one or more of the following parameters: airway pressure, exhaled volume, ventilation mode, type of breath, mean airway pressure, peak airway pressure, PEEP/CPAP pressure, plateau pressure, respiratory rate, I:E ratio, tidal volume, minute volume, and spontaneous minute volume.

As discussed above, display system 16 may display one or more graphical three-dimensional (3-D) waveform representations 40. A 3-D waveform representation 40 may include multiple instances of the waveform (e.g., a loop, curve, or other waveform) displayed simultaneously. The multiple waveform instances may be generated based on signals received from sensors 24 over a plurality of time periods, wherein each waveform instance 24 corresponds to one of the time periods. The time periods may or may not have a constant duration, depending on various factors such as the ventilation mode and/or type of breathing (e.g., spontaneous or assisted), for example. In some embodiments, each waveform instance corresponds to one breath.

In some embodiments or situations, waveform representations 40 may display raw, or unprocessed, data received from sensors 24. For example, flow and pressure data received from sensors 24 may be plotted as raw data in waveform representations 40, as opposed to plotting secondary parameters (e.g., dynamic patient compliance) that are calculated from such raw data. In other embodiments or situations, one or more such secondary parameters calculated from such raw data may be plotted in waveform representations 40.

Display device 32 may be partially or fully integrated with, or may be physically separate from, ventilation system 12. For example, display device 32 may comprise an integrated screen of a ventilator, CPAP, or BiPAP device, or a separate device such as a stand-alone monitoring device or a laptop computer.

Figure 2:
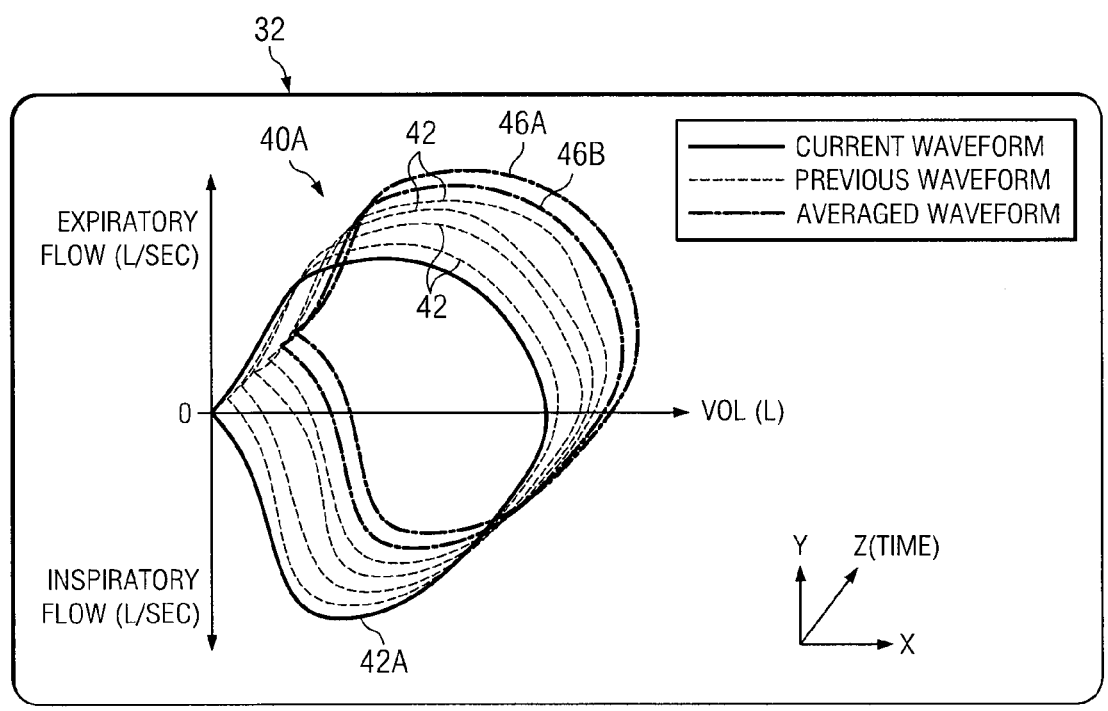
FIG. 2 illustrates an example three-dimensional waveform representation displayed by a display device, according to one embodiment of the disclosure.

FIG. 2 illustrates an example 3-D waveform representation 40A displayed by display device 32 according to one embodiment. Example waveform representation 40A represents a flow-volume loop waveform over time. Flow and volume variables are indicated in the x-y plane, and time is indicated in the z-dimension. Waveform representation 40A includes multiple waveform instances 42 displayed simultaneously. Waveform instances 42 may be generated based on flow and volume data received from flow and volume sensors 24 over a plurality of time periods such that each waveform instance 42 represents a flow-volume loop for a different time period. Each waveform instance 42 may correspond to one breath by patient 11.

As shown in FIG. 2, waveform instances 42 may be cascaded in the z-dimension to represent time. The most current waveform instance, indicated as instance 42A, is displayed in front, the next most recent waveform instance 42 is displayed behind the most recent waveform instance 42, and so on. As each new waveform instance 42 is displayed, the other waveform instances 42 move backwards in progression until they are eventually removed from waveform representation 40A. In this manner, 3-D waveform representation 40A may provide a graphical indication of changes in the flow-volume loop over time. Each new waveform instance 42A may be displayed, or "drawn," substantially instantaneously (e.g., after a breath is completed), in real time (e.g., moving clockwise or counter clock-wise around the flow-volume loop), or in any other suitable manner.

In some embodiments, the most current waveform instance 42A (or another particular instance 42) may have one or more different display characteristics than the individual waveform instances 42 in waveform representation 40A such that the current waveform instance 42A may be readily visually distinct from the waveform instances 42. As used herein, "display characteristics" may include any characteristic that may visually differentiate two displayed features, such as color, brightness, type of line (e.g., dashed vs. solid or flashing vs. non-flashing), and/or line thickness, for example.

In addition, particular portions of one or more waveform instance 42 may have one or more different display characteristics than other portions of such waveform instances 42 such that the different portions of such waveform instances 42 are readily distinguishable from each other.

Further, different types of waveform instances 42 may have one or more different display characteristics than other types of waveform instances 42 such that the different types of waveform instances 42 may be readily distinguishable from each other. For example, waveform instances 42 corresponding to alarm conditions may have one or more different display characteristics than other waveform instances 42. As another example, waveform instances 42 identified as outliers (e.g., where one or more parameter meets a threshold level) may have one or more different display characteristics than other waveform instances 42. As another example, waveform instances 42 corresponding to time periods before and after an operational change is implemented (e.g., a change implemented by control system 22, such as a change in ventilation mode, breath mode or breath type, pressure and/or flow of gas delivered by gas delivery system 20, etc.) may have one or more different display characteristics such that the two states may be readily distinguishable from each other. As another example, waveform instances 42 corresponding to different breath types (e.g., spontaneous, assisted, control, etc.) may have one or more different display characteristics such that the different breath types may be readily distinguishable from each other. As another example, waveform instances 42 corresponding to different respiratory maneuvers (e.g., an inspiratory pause maneuver) may have one or more different display characteristics.

In some embodiments, an average waveform may be calculated based on at least two waveform instances 42 and a corresponding average waveform graphic may be included in waveform representation 40A. In some embodiments, the average waveform may be calculated based on the waveform instances 42 currently displayed in waveform representation 40A, a subset of the waveform instances 42 currently displayed in waveform representation 40A, and/or one or more waveform instances 42 not currently displayed in waveform representation 40A. Any suitable number of waveform instances 42 may be included in the average waveform calculation.

In some embodiments, multiple average waveform graphics 46 may be displayed, each based on a different number of waveform instances 42. For example, in the embodiment shown in FIG. 2, waveform representation 40A includes a first average waveform graphic 46A representing an average of the 5 most recent waveform instances 42, and a second average waveform graphic 46B representing an average of the 50 most recent waveform instances 42.

In some embodiments, the number of waveform instances 42 and/or which particular waveform instances 42 (e.g., the ten most recent instances 42 or the instances 42 currently included in waveform representation 40A) to be included in the average waveform calculation for each average waveform graphic 46 may be selected and/or modified by a user via a user input associated with display system 16 and/or breathing assistance system 10. For example, display device 32 may be a touch screen GUI including an interface (e.g., displayed buttons or other selectable controls) allowing a user to select the number of waveform instances 42 to include in each average waveform calculation.

Each average waveform, and thus each average waveform graphic 46, may be automatically updated over time, e.g., after each new waveform instance 42 is available or after each new n waveform instances 42 are available, where n may be any suitable number.

Average waveform graphics 46 may be displayed at any suitable locations in waveform representation 40A. For example, average waveform graphics 46 may be displayed at the front or at the rear of the waveform instances 42 in waveform representation 40A. In some embodiments, average waveform graphics 46 may have one or more different display characteristics than the individual waveform instances 42 in waveform representation 40A such that the average waveform graphics 46 may be readily visually distinct from the waveform instances 42. In addition, average waveform graphics 46 may also be visually distinct from each other.

Figure 3:
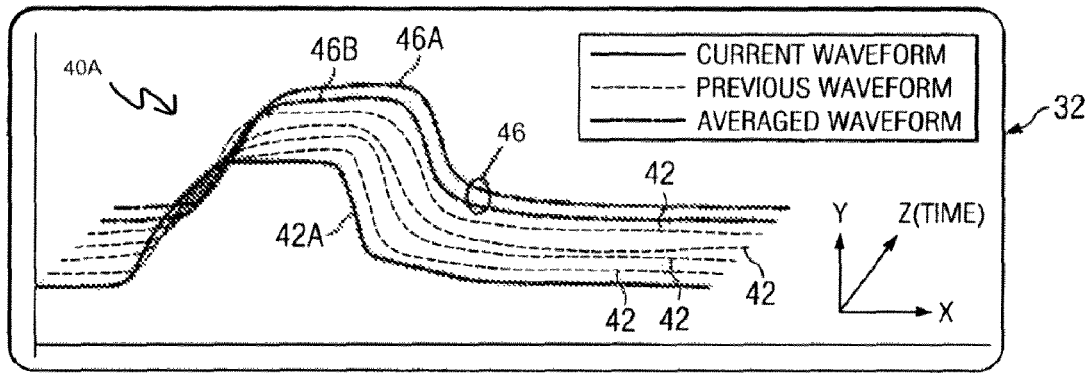
FIG. 3 illustrates another example three-dimensional waveform representation displayed by a display device, according to another embodiment of the disclosure.

FIG. 3 illustrates an example 3-D waveform representation 40B displayed by display device 32 according to one embodiment. Example waveform representation 40B represents a compliance curve waveform over time. Volume and compliance variables are indicated in the x-y plane, and time is indicated in the z-dimension. Waveform representation 40B includes multiple waveform instances 42 displayed simultaneously. Waveform instances 42 may be generated based on flow data received from sensors 24 over a plurality of time periods such that each waveform instance 42 represents a flow curve for a different time period. Each waveform instance 42 may correspond to one breath by patient 11.

Figure 4:
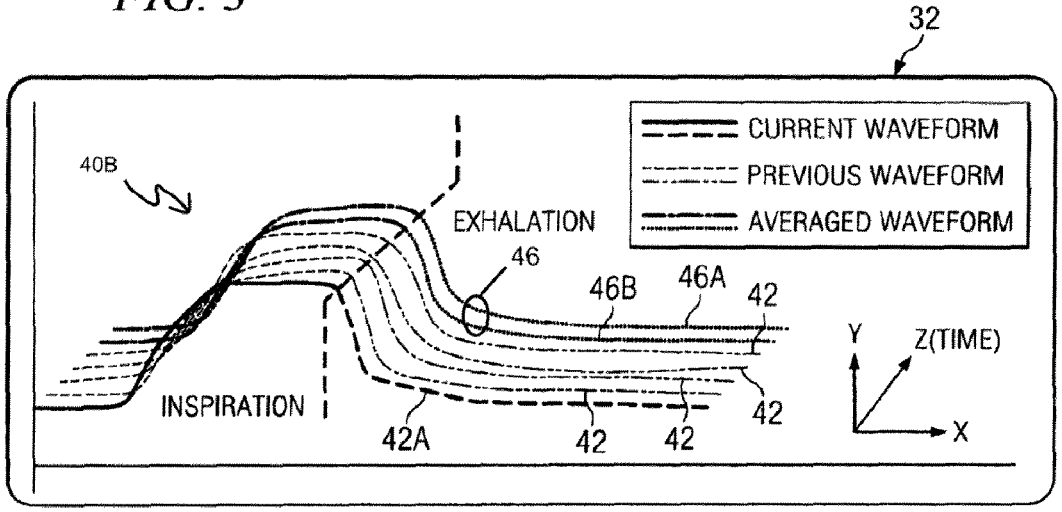
FIG. 4 illustrates another example three-dimensional waveform representation displayed by a display device, according to another embodiment of the disclosure.

FIG. 4 illustrates an example 3-D waveform representation 40C displayed by display device 32 according to one embodiment. Example waveform representation 40C may be similar to example waveform representation 40B shown in FIG. 3. However, FIG. 4 illustrates the use of different display characteristics for different phases of the breath cycle. In this embodiment, different colors are used to distinguish the inspiration phase from the exhalation phase of the breath cycle for each waveform instance 42.

In some embodiments, various user interfaces may be provided to allow a user to select, configure and/or modify various settings regarding waveform representation(s) 40 displayed by display device 32. For example, user interfaces may allow a user to select, configure and/or modify one or more of the following:

The number and/or type of waveform representation 40 displayed by display device 32;

The number of waveform instances 42 displayed in each waveform representation 40;

The number and/or type of average waveform graphics 46 to be displayed;

The number of waveform instances 42 and/or particular waveform instances 42 to be included in the average waveform calculation for each average waveform graphics 46; and/or Display characteristics settings: e.g., the user may be allowed to set one or more display characteristics settings for various types and/or portions of waveform instances 42, such as those discussed above regarding FIG. 2.

In addition, user interfaces may allow a user to configure and/or adjust the appearance of waveform representation 40 on display device 32. For example, user interfaces may allow the user to:

Set and/or adjust the scale of waveform representation 40 along one, two, or three dimensions;

Rotate the waveform representation 40 about one or more axes in one or more planes; and/or Zoom the waveform representation 40 in and out.

Such user interfaces allowing a user to select, configure, and/or modify any of such parameters (and/or other parameters) regarding one or more waveform representations 40 may be associated with display system 16 or ventilation system 12. For example, one or more user interfaces may be physical interfaces (e.g., physical buttons, knobs, or switches) provided by ventilation system 12. As another example, one or more user interfaces may be provided by a graphical user interface (GUI), such as a touch screen display (e.g., on the same display as the waveform representation or representations).

Figure 5:
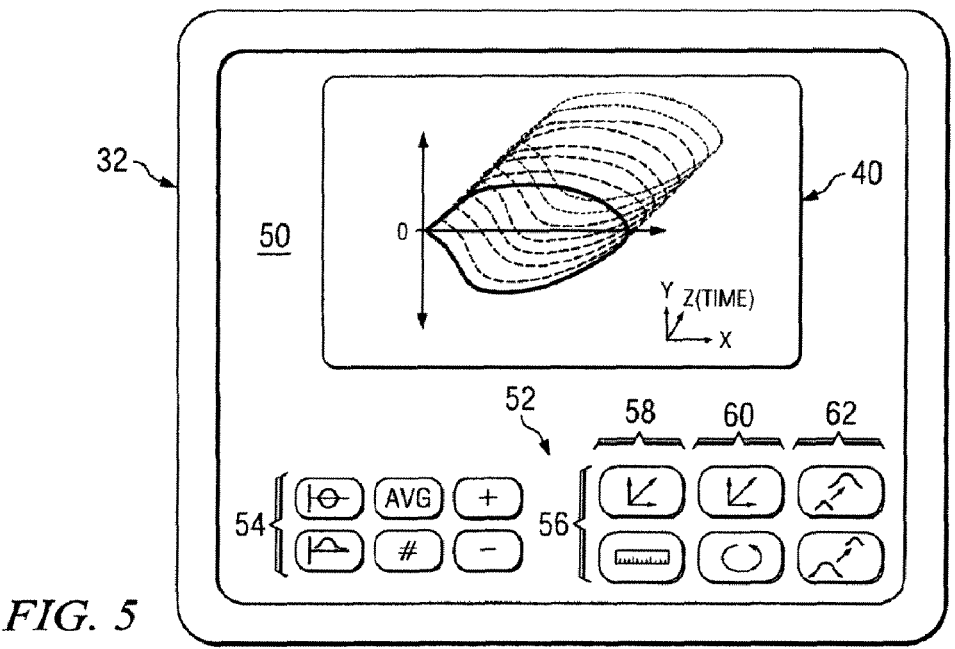
FIG. 5 illustrates an example GUI display displayed by display device, according to one embodiment of the disclosure.

FIG. 5 illustrates an example GUI display 50 displayed by display device 32, according to one embodiment. GUI display 50 may include one or more waveform representations 40 and one or more user interface buttons 52 allowing a user to select, configure and/or modify various parameters regarding waveform representations 40. In this example embodiment, user interface buttons 52 include a set of configuration buttons 54 and a set of view buttons 56.

Configuration buttons 54 may include one or more buttons for configuring: (a) the number and/or type of waveform representation 40 displayed by display device 32; (b) the number of waveform instances 42 displayed in each waveform representation 40; (c) the number and/or type of average waveform graphics 46 to be displayed; (d) the number of waveform instances 42 and/or particular waveform instances 42 to be included in the average waveform calculation for each average waveform graphics 46; and/or (e) various display characteristics settings for various types and/or portions of waveform instances 42, such as those discussed above regarding FIG. 2.

View buttons 56 may include scale buttons 58, rotation buttons 60, and zoom buttons 62. Scale buttons 58 may allow a user to select a dimension (e.g., x, y, or z) and setting the scale for that dimension. Rotation buttons 60 may allow a user to select an axis of rotation and rotate waveform representation 40 about that axis. In some embodiments, rotation buttons 60 may allow a user to rotate waveform representation 40 around three axes corresponding to the three dimensions (x, y, and z) and/or one or more other axes. Zoom buttons 62 may allow a user to zoom waveform representation 40 in and out. In some embodiments, zoom buttons 62 may allow a user to select a region or area of waveform representation 40 and zoom in or out on that region or area. Thus, for example, the user may analyze a particular portion of the breathing cycle. View buttons 56 may include any other buttons or user interfaces to allow a user to manipulate the appearance of waveform representation 40 in three-dimensional space.

GUI display 50 may include any other user interfaces and/or display any other data regarding the patient's breathing patterns and/or the operation of ventilation system 12. For example, GUI display 50 may display any one or more of the following parameters: airway pressure, exhaled volume, ventilation mode, type of breath, mean airway pressure, peak airway pressure, PEEP/CPAP pressure, plateau pressure, respiratory rate, I:E ratio, tidal volume, minute volume, and spontaneous minute volume.

It will be appreciated that while the disclosure is particularly described in the context of breathing assistance systems, the apparatuses, techniques, and methods disclosed herein may be similarly applied in other contexts. Additionally, it should be understood that various changes, substitutions and alterations can be made herein without departing from the spirit and scope of the disclosure as illustrated by the following claims.

What is claimed is:

1. An apparatus configured to display a three-dimensional representation of a waveform for a breathing assistance system, comprising:
   a processor configured to:
      receive signals from one or more sensors over a plurality of breaths; and
      generate multiple instances of a two-dimensional waveform based on the received signals, each instance corresponding to one of the plurality of breaths; and
   a display device configured to cooperate with the processor to simultaneously display graphical representations of the multiple instances of the two-dimensional waveform, the multiple instances of the two-dimensional waveform being graphically offset from each other to create a three-dimensional representation of the multiple waveform instances over time.

2. An apparatus according to claim 1, wherein the three-dimensional representation includes at least five instances of the two-dimensional waveform displayed simultaneously.

3. An apparatus according to claim 1, wherein each instance of the two-dimensional waveform indicates at least one characteristic of gas delivered by a breathing assistance apparatus.

4. An apparatus according to claim 1, wherein each instance of the two-dimensional waveform comprises a loop.

5. An apparatus according to claim 1, wherein instance of the two-dimensional waveform comprises a curve.

6. An apparatus according to claim 1, wherein the three-dimensional representation provides a graphical indication of changes in the two-dimensional waveform over time.

7. An apparatus according to claim 1, wherein each instance of the two-dimensional waveform corresponds to one breath.

8. An apparatus according to claim 1, wherein:
   the processor is operable to calculate an average waveform based on at least two instances of the waveform; and
   the three-dimensional representation includes an average waveform graphic indicating the calculated average waveform.

9. An apparatus according to claim 8, wherein the average waveform graphic is automatically updated over time.

10. An apparatus according to claim 8, wherein the average waveform graphic is displayed using a different display characteristic than the multiple instances of the waveform in the three-dimensional representation of the waveform such that the average waveform graphic is visually distinct from the multiple instances of the waveform.

11. An apparatus according to claim 10, wherein the display characteristic is selected from the group consisting of color, brightness, line thickness, and dashed line versus continuous line.

12. An apparatus according to claim 8, further comprising a user interface allowing a user to select the number of instances of the waveform to include in the average waveform calculation.

13. An apparatus according to claim 1, further comprising a user interface allowing a user to select a time duration that defines the number of instances of the waveform to include in the average waveform calculation.

14. An apparatus according to claim 1, further comprising a user interface allowing a user to select the number of instances of the waveform to include in the three-dimensional representation of the waveform.

15. An apparatus according to claim 1, further comprising a user interface allowing a user to select a time duration to display using the three-dimensional representation of the waveform.

16. An apparatus according to claim 1, wherein the most recent or current instance of the waveform is displayed using a different display characteristic than other instances of the waveform in the three-dimensional representation of the waveform such that the most recent or current instance is visually distinct from the other instances of the waveform.

17. An apparatus according to claim 16, wherein the display characteristic is selected from the group consisting of color, brightness, line thickness, and dashed line versus continuous line.

18. An apparatus according to claim 1, wherein:
   each instance of the two-dimensional waveform corresponds to a breath, each breath including an inspiratory phase and an expiratory phase, each instance of the two-dimensional waveform including an inspiratory portion corresponding to the inspiratory phase of the breath and an expiratory portion corresponding to the expiratory phase of the breath; and
   for at least one displayed instance of the two-dimensional waveform, the inspiratory portion is displayed using a different display characteristic than expiratory portion such that the inspiratory portion is visually distinct from the expiratory portion.

19. An apparatus according to claim 18, wherein the display characteristic is selected from the group consisting of color, brightness, line thickness, and dashed line versus continuous line.

20. An apparatus according to claim 1, wherein the three-dimensional representation of the waveform can be rotated.

21. An apparatus according to claim 1, wherein the three-dimensional representation of the waveform can be zoomed in or out.

22. An apparatus according to claim 1, wherein the multiple instances of the two-dimensional waveform are displayed relative to each other in a cascading manner.

23. An apparatus according to claim 1, wherein the three-dimensional representation of the waveform is automatically updated such that newer instances of the two-dimensional waveform replace older instances of the two-dimensional waveform in the three-dimensional representation.

24. A display device configured to display a graphical three-dimensional representation of a two-dimensional waveform over time, the three-dimensional representation including graphical representations of multiple instances of the two-dimensional waveform displayed simultaneously, wherein the multiple instances of the two-dimensional waveform are generated based on signals from one or more sensors over a plurality of breaths, each instance corresponding to one of the plurality of breaths, and wherein the multiple instances of the two-dimensional waveform are graphically offset from each other to provide the three-dimensional representation of the multiple waveform instances over time.

25. Logic instructions encoded in computer-readable media and when executed by a processor, operable to:
   receive signals from one or more sensors over a plurality of breaths;
   generate multiple instances of a two-dimensional waveform based on the received signals, each instance corresponding to one of the plurality of breaths; and
   cause the simultaneous display of graphical representations of the multiple instances of the two-dimensional waveform, the multiple instances of the two-dimensional waveform being graphically offset from each other to create a three-dimensional representation of the multiple waveform instances over time.

26. A breathing assistance device configured to display a three-dimensional representation of a waveform over time, comprising:

processing means for generating waveforms, the processing means configured to:

receive signals from one or more sensors over a plurality of breaths;

generate multiple instances of a two-dimensional waveform based on the received signals, each instance corresponding to one of the plurality of breaths; and display means for cooperating with the processing means to simultaneously display graphical representations of the multiple instances of the two-dimensional waveform, the multiple instances of the two-dimensional waveform being graphically offset from each other to create a three-dimensional representation of the multiple waveform instances over time.

* * * * *